(12) United States Patent
Bethan et al.

(10) Patent No.: US 8,216,847 B2
(45) Date of Patent: *Jul. 10, 2012

(54) MEANS AND METHOD FOR PREDICTING DIABETES

(75) Inventors: Bianca Bethan, Berlin (DE); Kristina Busch, Berlin (DE); Jan C Wiemer, Berlin (DE); Martijn Gipmans, Potsdam (DE); Edgar Leibold, Berlin (DE); Jochen Spranger, Kleinmachnow (DE); Thomas Bobbert, Berlin (DE); Andreas Friedrich Hermann Pfeiffer, Kleinmachnow (DE)

(73) Assignee: Metanomics GmbH, Berlin (DE)

( * ) Notice: Subject to any disclaimer, the term of this patent is extended or adjusted under 35 U.S.C. 154(b) by 168 days.

This patent is subject to a terminal disclaimer.

(21) Appl. No.: 12/293,587

(22) PCT Filed: Mar. 21, 2007

(86) PCT No.: PCT/EP2007/052692
§ 371 (c)(1),
(2), (4) Date: Oct. 14, 2008

(87) PCT Pub. No.: WO2007/110358
PCT Pub. Date: Oct. 4, 2007

(65) Prior Publication Data
US 2010/0236321 A1 Sep. 23, 2010

(30) Foreign Application Priority Data

Mar. 24, 2006 (EP) .................................... 06111705
Sep. 7, 2006 (EP) .................................... 06120273

(51) Int. Cl.
*G01N 33/48* (2006.01)
*G01N 33/68* (2006.01)

(52) U.S. Cl. ............... 436/63; 436/71; 436/86; 436/89; 436/95; 436/161; 436/173

(58) Field of Classification Search .............. 436/63, 436/71, 86, 89, 94, 95, 161, 173; 252/408.1; 702/19; 250/282
See application file for complete search history.

(56) References Cited

U.S. PATENT DOCUMENTS

| | | | |
|---|---|---|---|
| 4,540,884 A | 9/1985 | Stafford et al. | |
| 4,810,640 A | 3/1989 | Nakamura et al. | |
| 5,194,448 A | 3/1993 | Coupland et al. | |
| 5,397,894 A | 3/1995 | Wells et al. | |
| 5,871,949 A | 2/1999 | Ebinuma et al. | |
| 5,965,449 A | 10/1999 | Novak | |
| 6,153,419 A | 11/2000 | Aisaka et al. | |
| 6,268,166 B1 | 7/2001 | Kojima et al. | |
| 6,309,852 B1 | 10/2001 | Tazoe et al. | |
| 6,448,029 B1 | 9/2002 | Tazoe et al. | |
| 2002/0068310 A1 | 6/2002 | Sasaki et al. | |
| 2004/0132819 A1* | 7/2004 | Auestad et al. | 514/560 |
| 2005/0108788 A1* | 5/2005 | Osumi et al. | 800/281 |
| 2005/0177397 A1* | 8/2005 | Kane | 705/2 |
| 2005/0202521 A1 | 9/2005 | Crum | 435/26 |
| 2009/0155826 A1* | 6/2009 | Hu et al. | 435/11 |
| 2010/0163720 A1 | 7/2010 | Bethan et al. | |
| 2011/0172926 A1* | 7/2011 | Watkins | 702/19 |

OTHER PUBLICATIONS

Magnes et al. Analytical Chemistry, vol. 77, 2005, pp. 2889-2894.*
http://en.wikipedia.org/wiki/Eicosenoic_acid, printed on Mar. 30, 2011.*
Webpage from www.chemicalbook.com/ChemicalProductProperty_EN_CB9769294.htm, copyright 2010.*
Granado, F., et al., "Carotenoids, Retinol and Tocopherols in Patients with Insulin-Dependent Diabetes Mellitus and Their Immediate Relatives", Clinical Science, vol. 94, (1998), pp. 189-195.
Coyne, T., et al., "Diabetes Mellitus and Serum Carotenoids: Findings of a Population-Based Study in Queensland, Australia", American Journal of Clinical Nutrition, vol. 82, No. 3, (2005), pp. 685-693.
Ford, E.S. et al., "Diabetes Mellitus and Serum Carotenoids: Findings from the Third National Health and Nutrition Examination Survey", American Journal of Epidemiology, vol. 149, No. 2, (1999), pp. 168-176.
Hao, Z., et al., "Simultaneous Quantification of alpha-tocopherol and Four Major Carotenoids in Botanical Materials by Normal Phase Liquid Chromatography—Atmospheric Pressure Chemical Ionization—Tandem Mass Spectrometry", Journal of Chromatography A., vol. 1094, (2005), pp. 83-90.
Niessen, W.M.A., et al., "Liquid Chromatography—Mass Spectrometry General Principles and Instrumentation", Journal of Chromatography A, vol. 703, (1995), pp. 37-57.
Pitkänen, E., et al., "Enzymatic Determination of Unbound D-Mannose in Serum", European Journal of Clin. Chem. and Clin. Biochem., vol. 35, No. 10, (1997), pp. 761-766.

(Continued)

Primary Examiner — Maureen Wallenhorst
(74) Attorney, Agent, or Firm — Connolly Bove Lodge & Hutz, LLP

(57) ABSTRACT

The present invention relates to a method for diagnosing a predisposition for diabetes, comprising determining a metabolite in a test sample of a subject suspected to have a predisposition for diabetes and comparing the metabolite to a reference to diagnose the, predisposition for diabetes. Moreover, the present invention encompasses a collection of metabolites, a data collection comprising characteristic values of metabolites and a storage medium comprising the data collection. The present invention also relates to a system comprising methods or devices for comparing characteristic values of metabolites of a sample operatively linked to a data storage medium. Additionally, diagnostic methods or devices comprising a metabolite and its use for manufacture of the diagnostic method or device for diagnosing a predisposition for diabetes are provided, along with a method for identifying diabetes-related metabolites.

23 Claims, No Drawings

OTHER PUBLICATIONS

Lee. W., et al., "Ascorbic Acid Determination with an Automated Enzymatic Procedure", Clinical Chemistry, vol. 43, No. 1, (1997), pp. 154-157.

La Du, B.N., et al., "A Quantitative Micromethod for the Determination of Phenylalanine and Tyrosine in Blood and its Application in the Diagnosis of Phenylketonuria in Infants", Pediatrics, vol. 31, No. 1, Part 1, (1963), pp. 39-46.

Sumi, T., et al., "The Enzymatic Spectrofluorimetric Determination of Uric Acid in Microsamples of Plasma by Using p-Hydroxyphenyl-Acetic Acid as a Fluorophor", Clinica Chimica Acta, vol. 73, (1976), pp. 233-239.

Thiele, J.J., et al., "Ascorbic Acid and Urate in Human Seminal Plasma: Determination and Interrelationships with Chemiluminescence in Washed Semen", in Human Reproduction, Oxford University Press, (1995), pp. 110-115.

Carchon, H.A., et al., "Determination of D-Mannose in Serum by Capillary Electrophoresis", Clinical Chemistry, vol. 47, No. 7, (2001), pp. 1319-1321.

Kyaw, A., "A Simple Colorimetric Method for Ascorbic Acid Determination in Blood Plasma", Clinica Chimica Acta, vol. 86, (1978), pp. 153-157.

Nathan, D., et al., "Impaired Fasting Glucose and Impaired Glucose Tolerance", Diabetes Care, vol. 30, No. 3, (2007), pp. 753-759.

Niwa, T., et al., "Quantification of Serum 1,5-Anhydroglucitol in Uremic and Diabetic Patients by Liquid Chromatography/Mass Spectrometry", Clin. Chem., vol. 40, No. 2, (1994), pp. 260-264.

Pitkanen, E., "Mannose, Mannitol, Fructose and 1.5-Anhydroglucitol Concentrations Measured by Gas Chromatography/Mass Spectrometry in Blood Plasma of Diabetic Patients", Clinical Chimica Acta, vol. 251, (1996), pp. 91-103.

Pitkanen, E., "Serum 1,5-anhydroglucitol in Normal Subjects and in Patients with Insulin-Dependent Diabetes Mellitus", Scand. J. Clin. and Lab. Investigation, vol. 42, (1982), pp. 445-448.

Tanabe, T., et al., "Fully Automated Flow-Injection System for Quantifying 1,5-Anhydro-d-Glucitol in Serum", Clin. Chem., vol. 40, No. 11, (1994), pp. 2006-2012.

Watanabe, K., et al., "Different Effects of Two alpha-glucosidase Inhibitors, Acarbose and Voglibose, on Serum 1,5-anhydroglucitol (1,5AG) Level", Journal of Diabetes and its Complications, vol. 18, (2004), pp. 183-186.

Yamanouchi, T., et al., "Serum 1,5-anhydroglucitol (1,5 AG): New Clinical Marker for Glycemic Control", Diabetes Research and Clinical Practice, vol. 24 Suppl., (1994), pp. S261-S268.

Deng, C., et al., "Rapid Determination of Acetone in Human Blood by Derivatization With Pentafluorobenzyl Hydroxylamine Followed by Headspace Liquid-Phase Microextraction and Gas Chromatography/Mass Spectrometry", Rapid Communications in Mass Spectrometry, vol. 19, (2005), pp. 647-653.

Jellum, E., et al., "Combined Use of Gas Chromatography, Mass Spectrometry, and Computer in Diagnosis and Studies of Metabolic Disorders", Clinical Chemistry, vol. 18, No. 8, (1972), pp. 800-809.

Lovejoy, J. C., et al., "Effects of Diets Enriched in Saturated (Palmitic), Monounsaturated (Oleic), or *trans* (Elaidic) Fatty Acids on Insulin Sensitivity and Substrate Oxidation in Healthy Adults", Diabetes Care, vol. 25, No. 8, (2002), pp. 1283-1288.

Odani, H., et al., "Identification of $N^{\omega}$-Carboxymethylarginine, a New Advanced Glycation Endproduct in Serum Proteins of Diabetic Patients: Possibility of a New Marker of Aging and Diabetes", Biochemical and Biophysical Research Communications, vol. 285, (2001), pp. 1232-1236.

Polidori, M.C., et al., "Plasma Levels of Lipophilic Antioxidants in Very Old Patients with Type 2 Diabetes", Diabetes/Metabolism Research and Reviews, vol. 16, (2000), pp. 15-19.

Sinclair, A.J., et al., "Low Plasma Ascorbate Levels in Patients with Type 2 Diabetes Mellitus Consuming Adequate Dietary Vitamin C", Diabetic Medicine, vol. 11, (1994), pp. 893-898.

Som, S., et al., "Ascorbic Acid Metabolism in Diabetes Mellitus", Metabolism, vol. 30, No. 6, (1981), pp. 572-577.

Yamada, H., et al., "Lymphocyte and Plasma Vitamin C Levels in Type 2 Diabetic Patients With and Without Diabetes Complications", Diabetes Care, vol. 27, No. 10, (2004), pp. 2491-2492.

* cited by examiner

MEANS AND METHOD FOR PREDICTING DIABETES

RELATED APPLICATIONS

This application is a national stage application (under 35 U.S.C. 371) of PCT/EP2007/052692, filed Mar. 21, 2007, which claims benefit of European application 06111705.7 filed Mar. 24, 2006 and European application 06120273.5, filed Sep. 7, 2006.

The present invention relates to a method for diagnosing a predisposition for diabetes comprising determining at least one metabolite in a test sample of a subject suspected to have a predisposition for diabetes and comparing said at least one metabolite to a reference, whereby a predisposition for diabetes is to be diagnosed. Moreover, the present invention encompasses a collection of metabolites, a data collection comprising characteristic values of metabolites and a storage medium comprising said data collection. Furthermore, the present invention also relates to a system comprising means for comparing characteristic values of metabolites of a sample operatively linked to a data storage medium. Further encompassed by the present invention are diagnostic means comprising at least one metabolite and the use of said at least one metabolite for the manufacture of diagnostic means for diagnosing a predisposition for diabetes. Finally, the present invention pertains to a method for identifying diabetes-related metabolites.

The prevalence of diabetes mellitus has reached about 6% in the industrialised world and will increase up to 366 million affected people in 2030 worldwide. The most frequently reason (type), (about 90%) for diabetes in the world is accounted for type 2 diabetes, which has a multifactorial pathogenesis. The pathological sequence for type 2 diabetes entails many elements. It is believed to be mandatory to have a genetic predisposition that is currently poorly understood. Whether the diabetes phenotype then occurs is influenced by many environmental factors that share an ability to stress the glucose homeostasis system, either by causing or worsening insulin resistance or impairing insulin secretion. Of course many hormones are taking part in the regulation of glucose metabolism, but the key hormone is insulin. Normoglycaemia is maintained by the balanced interplay between insulin action and insulin secretion. Insulin is produced by the pancreatic β-cell which is able to regulate very fast to different glucose demands. The main reason for type 2 diabetes is an increasing insulin resistance. Therefore, insulin action normally decrease but initially the system is able to compensate this by an increasing β-cell function. At this time perhaps only an impaired fasting glucose or an impaired glucose tolerance in the OGTT could be measured. But over time the β-cell will be overstressed by increasing insulin resistance and glucose toxicity and a type 2 diabetes could be diagnosed.

Apart from direct medical problems by high or low blood sugar the main medical and socioeconomic burden of the disease is caused by the associated complications. The devastating complications of diabetes mellitus are mostly macrovascular and microvascular diseases like chronic renal failure, retinopathy, periphery and autonomic neuropathy or myocardial infarction. Therefore, cardiovascular morbidity in patients with type 2 diabetes is two to four times greater than that of non-diabetic people (Stumvoll et al., Type 2 diabetes: principles of pathogenesis and therapy, Lancet 2005).

In light of this mechanism, therapy of diabetes is currently based on monitoring the blood sugar levels and reducing an elevated level of blood sugar into a normal level by administration of exogenous insulin. To this end, exogenous insulin is injected into the blood. Alternatively, glucose levels in the blood may be regulated by nutritional diets and the exclusion of life-style risk factors, such as smoking, lack of exercise, high cholesterol levels, and an unstable body weight.

The Expert Committee of the ADA (American Diabetes Association) recognized an intermediate group of subjects whose glucose levels, although not meeting criteria for diabetes, are nevertheless too high to be considered normal. This group is defined as having fasting plasma glucose (FPG) levels >100 mg/dl (5.6 mmol/l) but <126 mg/dl (7.0 mmol/l) or 2-h values in the oral glucose tolerance test (OGTT) of >140 mg/dl (7.8 mmol/l) but <200 mg/di (11.1 mmol/l). Thus, the categories of FPG values are as follows:

FPG<100 mg/dl (5.6 mmol/l)=normal fasting glucose;
FPG 100-125 mg/dl (5.6-6.9 mmol/l)=IFG (impaired fasting glucose);
FPG>126 mg/dl (7.0 mmol/l)=provisional diagnosis of diabetes (the diagnosis must be confirmed, as described below).

The corresponding categories when the OGTT is used are the following:

2-h postload glucose <140 mg/dl (7.8 mmol/l)=normal glucose tolerance
2-h postload glucose 140-199 mg/dl (7.8-11.1 mmol/l)=IGT (impaired glucose tolerance)
2-h postload glucose >200 mg/dl (11.1 mmol/l)=provisional diagnosis of diabetes (the diagnosis must be confirmed, as described below).

Diagnosis of Diabetes Mellitus Type 2:
1. Symptoms of diabetes plus casual plasma glucose concentration >200 mg/dl (11.1 mmol/l). Casual is defined as any time of day without regard to time since last meal. The classic symptoms of diabetes include polyuria, polydipsia, and unexplained weight loss. Alternatively: 2. FPG>126 mg/dl (7.0 mmol/l). Fasting is defined as no caloric intake for at least 8 h. Alternatively: 3. 2-h postload glucose >200 mg/di (11.1 mmol/l) during an OGTT. The test should be performed as described by WHO, using a glucose load containing the equivalent of 75 g anhydrous glucose dissolved in water.

In the absence of unequivocal hyperglycemia, these criteria should be confirmed by repeat testing on a different day. The third measure (OGTT) is not recommended for routine clinical use.

(American Diabetes Association, Diagnosis and Classification of Diabetes Mellitus, Diabetes Care 2006) However, an increase in the blood sugar levels or a decrease in the available insulin are rather downstream developments in the development and progression of diabetes. Alternative diagnostic measures or diagnostic measures which would even identify individuals at risk before the early onset of the disease or at least in an early state of the disease are not yet available.

Accordingly, the technical problem underlying the present invention must be seen as the provision of means and methods for efficiently and reliably diagnosing a predisposition for diabetes. The technical problem is solved by the embodiments characterized in the claims and described herein below.

Accordingly, the present invention relates to a method for diagnosing a predisposition for diabetes comprising:
(a) determining at least one metabolite in a test sample of a subject suspected to suffer from diabetes or to have a predisposition therefor, said at least one metabolite being selected from the group consisting of: cryptoxanthin, 2-hydroxy-palmitic acid, triacylglyceride (C16:0,C18:1,C18:2), gondoic acid, tricosanoic acid, 5-Oxoproline; and (b) comparing the results of the determination in step (a) to a reference, whereby a predisposition for diabetes is to be diagnosed.

Each of said metabolites is a suitable biomarker by its own for the predisposition for diseases referred to herein. However, most preferably, a group of biomarkers including or consisting of the biomarkers of one of the aforementioned group is to be determined by the method of the present invention. A group of biomarkers consists, preferably, of at least two, at least three, at least four and, preferably, up to all of the aforementioned biomarkers.

The expression "method for diagnosing" as referred to in accordance with the present invention means that the method may essentially consist of the aforementioned steps or may include further steps. However, it is to be understood that the method, in a preferred embodiment, is a method carried out in vitro, i.e. not practised on the human or animal body. Diagnosing as used herein refers to assessing the probability according to which a subject will have a predisposition for the diseases referred to herein, i.e. diabetes. Diagnosis of a predisposition may sometimes be referred to as prognosis or prediction of the likelihood that a subject will develop the disease. As will be understood by those skilled in the art, such an assessment, although preferred to be, may usually not be correct for 100% of the subjects to be diagnosed. The term, however, requires that a statistically significant portion of subjects can be identified as having a predisposition for the diseases referred to herein. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, at least 95%. The p-values are, preferably, 0.2, 0.1, 0.05.

Diagnosing according to the present invention includes monitoring, confirmation, and classification of the predisposition for the relevant disease or its symptoms. Monitoring relates to keeping track of an already diagnosed predispostion (for the disease), or a complication, c.g. to analyze the progression of the disease, the influence of a particular treatment on the progression of disease or complications arising during the disease period or after successful treatment of the disease. Confirmation relates to the strengthening or substantiating a diagnosis already performed using other indicators or markers. Classification relates to allocating the diagnosis according to the strength or kind of symptoms into different classes, e.g. the diabetes types as set forth elsewhere in the description. Specifically, subjects can be, preferably, classified for different risk groups based on the metabolites and the kind of regulation as shown in the Tables, below. The metabolite biomarkers may be indicative for subjects having an increased risk for diabetes and falling into the risk group of impaired fasting glucose (IFG), impaired glucose tolerance (IGT) or both (IFG&IGT) as indicated in the Tables, below. Thus, preferably, the method of the present invention is a method for diagnosing whether a subject has a predisposition for diabetes or suffers from IFG, IGT or IFG&IGT based on the metabolites being associated with the said increased risk as listed in the accompanying Tables.

The term "diabetes" or "diabetes mellitus" as used herein refers to disease conditions in which the glucose metabolism is impaired. Said impairment results in hyperglycaemia. According to the World Health Organisation (WHO), diabetes can be subdivided into four classes. Type 1 diabetes is caused by a lack of insulin. Insulin is produced by the so called pancreatic islet cells. Said cells may be destroyed by an autoimmune reaction in Type 1 diabetes (Type 1 a). Moreover, Type 1 diabetes also encompasses an idiopathic variant (Type 1b). Type 2 diabetes is caused by an insulin resistance. Type 3 diabetes, according to the current classification, comprises all other specific types of diabetes mellitus. For example, the beta cells may have genetic defects affecting insulin production, insulin resistance may be caused genetically or the pancreas as such may be destroyed or impaired. Moreover, hormone deregulation or drugs may also cause Type 3 diabetes. Type 4 diabetes may occur during pregnancy. Preferably, diabetes as used herein refers to diabetes Type 2. According to the German Society for Diabetes, diabetes is diagnosed either by a plasma glucose level being higher than 110 mg/dl in the fasting state or being higher than 220 mg/dl postprandial. Further preferred diagnostic techniques are disclosed elsewhere in this specification. Further symptoms of diabetes are well known in the art and are described in the standard text books of medicine, such as Stedman or Pschyrembl.

The term "predisposition" as used herein means that a subject has not yet developed the disease or any of the aforementioned disease symptoms or other diagnostic criteria but, nevertheless, will develop the disease within a defined time window in the future (predictive window) with a certain likelihood. The predictive window is an interval in which the subject shall develop the disease or condition according to the predicted probability. The predictive window may be the entire remaining lifespan of the subject upon analysis by the method of the present invention. Preferably, however, the predictive window is an interval of one month, six months or one, two, three, four, five or ten years after the sample to be analyzed by the method of the present invention has been obtained. The likelihood for developing the diseases referred to herein shall be significantly larger for a subject having a predisposition than the likelihood of statistical appearance of diabetes mellitus within a given cohort of subjects. Preferably, for an individual subject the likelihood associated with a predisposition for developing diabetes is at least 30%, at least 40%, at least 50%, at least 60%, at least 70%, at least 80%, at least 90% or 100% or at least 1.5-times, 2-times, 3-times, 4-times, 5-times or 10-times increased compared with the average likelihood for a subject of a given cohort for developing diabetes. A cohort of subjects as referred to herein means a plurality of individual subjects which are of the same species and, preferably, are of the same or genetic background or ethnical group and, more preferably, also of the same age and gender.

The term "at least one metabolite" as used herein refers to a single metabolite or to a plurality of metabolites, i.e. preferably at least 2, 3, 4, 5, 10, 50, 100, 500, 1,000, 2,000, 3,000, 5,000 or 10,000 metabolites. It is to be understood that "metabolite" as used herein may be at least one molecule of said metabolite up to a plurality of molecules of the metabolite and that a plurality of metabolites means a plurality of chemically different molecules wherein for each metabolite at least one molecule up to a plurality of molecules may be present. A metabolite in accordance with the present invention encompasses all classes of organic or inorganic chemical compounds including those being comprised by biological material such as organisms. Preferably, the metabolite in accordance with the present invention is a small molecule compound. More preferably, in case a plurality of metabolites is envisaged, said plurality of metabolites representing a metabolome, i.e. the collection of metabolites being comprised by an organism, an organ, a tissue or a cell at a specific time and under specific conditions.

The metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including e.g. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da.

It will be understood that in addition to the aforementioned metabolites or groups of metabolites, an additional metabolite or a group of additional metabolites may be determined by the method of the present invention as well. Said additional metabolite or group thereof may include metabolites known to be associated with diabetes or predisposition for diabetes. Preferably, said additional metabolite is Glucose.

Other preferred metabolites to be determined together, i.e. either simultaneously or consecutively, with the aforementioned metabolites or groups of metabolites are metabolites selected from the group consisting of:
(i) a long-chain saturated fatty acid, preferably, Lignoceric acid (C24:0), Melissic acid (C30:0), or Tricosanoic acid (C23:0),
(ii) a poly-unsaturated fatty acid, preferably, Docosahexaenoic acid (C22:cis[4,7,10,13,16,19]6), Eicosapentaenoic acid (C20:cis[5,8,11,14,17]5), Arachidonic acid (C20:cis-[5,8,11,14]4), Linoleic acid (C18:cis[9,12]2), or Linolenic acid (C18:cis[9,12,15]3),
(iii) an amino acid, preferably, Lysine, Alanine, Threonine, Tryptophane, Valine, Isoleucine, Leucine, Cysteine, Methionine, Tyrosine, Phenylalanine, Glycine, Proline, or Glutamine,
(iv) an antioxidant, preferably, Ascorbic acid, Coenzyme Q10, or alpha-Tocopherol,
(v) a metabolite of the Citric Acid Cycle, preferably, Pyruvate, Citrate, or Malate,
(vi) a metabolite of the Urea Cycle, preferably, Urea, Citrulline, Succinate, or Ornithine,
(vii) Mannose, alpha-Ketoisocaproic acid, Glycerol, lipid fraction, or 3-Hydroxybutyric acid,
(viii) glucose.

A "long chain saturated fatty acid" as referred to in accordance with the present invention encompasses, preferably, C18 to C30 fatty acids wherein the numbers "18" and "30" indicate the number of carbon atoms in the fatty acid chain. More preferably, it relates to C20 to C30 fatty acids, and, most preferably to Lignoceric acid (C24:0), Melissic acid (C30:0), or Tricosanoic acid (C23:0).

A "poly-unsaturated fatty acid" as used herein means a fatty acid comprising more than one unsaturated carbon bond. Poly unsaturated fatty acids preferably envisaged by the present invention are C18 to C22 poly unsaturated fatty acids, and, most preferably, Docosahexaenoic acid (C22:cis[4,7,10,13,16,19]6), Eicosapentaenoic acid (C20:cis[5,8,11,14,17]5), Arachidonic acid (C20:cis-[5,8,11,14]4), Linoleic acid (C18:cis[9,12]2), or Linolenic acid (C18:cis[9,12,15]3).

The term "amino acid" as used herein encompasses the natural occurring amino acids as well as derivatives thereof. The naturally occurring amino acids are well known in the art and are described in standard text books of biochemistry. More preferably, the term relates to Lysine, Alanine, Threonine, Tryptophane, Valine, Isoleucine, Leucine, Cysteine, Methionine, Tyrosine, Phenylalanine, Glycine, Proline, or Glutamine.

The term "antioxidant" as used herein encompasses compounds which are capable of preventing oxidation in a subject. Preferably, the term relates to naturally occurring metabolites which may serve as coenzymes in the cell of a subject or which are vitamins including those which need to be exogenously supplied. More preferably, an anti-oxidant according to the present invention is Ascorbic acid, Coenzyme Q10, or alpha-Tocopherol.

The term "a metabolite of the Citric Acid Cycle" or "a metabolite of the Urea Cycle" relates to the products, intermediates and reactants which are synthesized or used as substrates in the aforementioned well known biochemical conversion cascades. Those products, intermediates or reactants are described in the biochemical standard text books and are well known to those skilled in the art. Preferably, Pyruvate, Citrate, or Malate are a metabolite of the Citric Acid Cycle. Urea, Citrulline, Succinate, or Ornithine are, preferably, a metabolite of the Urea Cycle referred to herein.

Preferably, a group of biomarkers is determined in accordance with the method of the present invention. More preferably, said group consists of biomarkers from different metabolite groups specified above under (i) to (vii). Most preferably, at least one metabolite of at least two, at least three, at least four, at least five, at least six or all of the aforementioned groups (i) to (vii) is to be determined. It has been found that the members of the aforementioned metabolite classes provide supportive biomarkers for diagnosing diabetes or a predisposition for diabetes. Moreover, a combination of the aforementioned metabolite classes provides even more superior and reliable results.

Also preferably, in addition to the aforementioned supportive metabolites or groups of supportive metabolites at least one supportive metabolite is determined selected from any of the following groups consisting of: 3-hydroxybutyric acid, alanine, alpha-ketoisocaproic acid, alpha-tocopherol, arginine, ascorbic acid, aspargine, beta-carotene, cholestenol, citrate, citrulline, creatinine, eicosapentaenoic acid (C20:cis[5,8,11,14,17]5), folate, glucose, glucose-1-phosphate, glutamate, glutamine, glyceric acid, glycerol-3-phosphate, glycine, isoleucine, lactate, leucine, malate, mannose, methionine, myo-inositol, ornithine, palmitic acid, phospholipids, pregnenolone sulfate, stearic acid, succinate, threonic acid, threonine, triacylglycerides, tryptophane, uric acid, and valine.

More preferably, the at least one supportive metabolite is selected from the group consisting of: tryptophane, alanine, leucine, palmitic acid, eicosatrienoic acid, glycerophospholipids, isoleucine, eicosatrienoic acid, tryptophane, lignoceric acid, linoleic acid, serine, tyrosine, linoleic acid, pregnenolone sulfate, aspartate, arachidonic acid, and succinate. Most preferably, the subject in said case is a male.

More preferably, the at least one supportive metabolite is selected from the group consisting of: alanine, palmitic acid, isoleucine, eicosatrienoic acid, uric acid, stearic acid, and serine. Most preferably, the subject in said case is a female.

Each of said metabolites is a suitable supportive biomarker by its own for the predisposition of the diseases referred to herein. However, most preferably, a group of supportive biomarkers including or consisting of the biomarkers of one of the aforementioned groups is to be determined by the method of the present invention. A group of biomarkers consists, preferably, of at least two, at least three, at least four and, preferably, up to all of the aforementioned supportive biomarkers.

The supportive metabolites referred to before will, preferably, also be compared to suitable reference results as specified elsewhere herein. The result of the said comparison will be further supportive for the finding as to whether the subject will have a predisposition for the diseases referred to herein or not. Preferred reference results, values for changes of the relative amounts and indications for the kind of regulation are to be found in the accompanying Examples, below.

The term "test sample" as used herein refers to samples to be used for the diagnosis of a predisposition for diabetes by the method of the present invention. Said test sample is a biological sample. Samples from biological sources (i.e. biological samples) usually comprise a plurality of metabolites. Preferred biological samples to be used in the method of the present invention are samples from body fluids, preferably, blood, plasma, serum, lymph, sudor, saliva, tears, sperm, vaginal fluid, faeces, urine or cerebrospinal fluid, or samples derived, e.g., by biopsy, from cells, tissues or organs. This also encompasses samples comprising subcellular compartments or organelles, such as the mitochondria, Golgi network or peroxisomes. Moreover, biological samples also encompass gaseous samples, such as volatiles of an organism. Biological samples are derived from a subject as specified elsewhere herein. Techniques for obtaining the aforementioned different types of biological samples are well known in the art. For example, blood samples may be obtained by blood taking while tissue or organ samples are to be obtained, e.g., by biopsy.

The aforementioned samples are, preferably, pre-treated before they are used for the method of the present invention. As described in more detail below, said pre-treatment may include treatments required to release or separate the compounds or to remove excessive material or waste. Suitable techniques comprise centrifugation, extraction, fractioning, purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to the said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The term "subject" as used herein relates to animals, preferably to mammals such as mice, rats, sheep, dogs, cats, horses, monkeys, or cows and, also preferably, to humans. Other animals which may be diagnosed applying the method of the present invention are birds or reptiles. A subject suspected to suffer from diabetes or to have a predisposition therefor as used herein refers to a subject which shows, preferably, symptoms or clinical signs or parameters indicative for diabetes. However, the term also relates to an apparently healthy subject, i.e. a subject not exhibiting any of the aforementioned symptoms, clinical signs or parameters. Apparently healthy subjects may by investigated by the method of the present invention as a measure of preventive care or for population screening purposes.

The term "determining said at least one metabolite" as used herein refers to determining at least one characteristic feature of the at least one metabolite comprised by the sample referred to herein. Characteristic features in accordance with the present invention are features which characterize the physical and/or chemical properties including biochemical properties of a metabolite. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a metabolite by standard operations, e.g., mathematical calculations such as multiplication, division or logarithmic calculus. Most preferably, the at least one characteristic feature allows the determination and/or chemical identification of the said at least one metabolite.

The at least one metabolite comprised by a test sample may be determined in accordance with the present invention quantitatively or qualitatively. For qualitative determination, the presence or absence of the metabolite will be determined by a suitable technique. Moreover, qualitative determination may, preferably, include determination of the chemical structure or composition of the metabolite. For quantitative determination, either the precise amount of the at least one metabolite present in the sample will be determined or the relative amount of the at least one metabolite will be determined, preferably, based on the value determined for the characteristic feature(s) referred to herein above. The relative amount may be determined in a case were the precise amount of a metabolite can or shall not be determined. In said case, it can be determined whether the amount in which the metabolite is present is enlarged or diminished with respect to a second sample comprising said metabolite in a second amount. Quantitatively analysing a metabolite, thus, also includes what is sometimes referred to as semi-quantitative analysis of a metabolite.

Moreover, determining as used in the method according to the present invention, preferably, includes using a compound separation step prior to the analysis step referred to before. Preferably, said compound separation step yields a time resolved separation of the metabolites comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention. Suitable devices for such determination of metabolites are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference. As an alternative or in addition to mass spectrometry techniques, the following techniques may be used for compound determination: nuclear magnetic resonance (NMR), magnetic resonance imaging (MRI), Fourier transform infrared analysis (FT-IR), ultra violet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado. The method of the present invention shall be, preferably, assisted by automation. For example, sample processing or pre-treatment can be automated by robotics. Data processing and comparison is, preferably, assisted by suitable computer programs and databases. Automation as described herein before allows using the method of the present invention in high-throughput approaches.

Moreover, the at least one metabolite can also be determined by a specific chemical or biological assay. Said assay shall comprise means which allow to specifically detect the at least one metabolite in the sample. Preferably, said means are capable of specifically recognizing the chemical structure of the metabolite or are capable of specifically identifying the metabolite based on its capability to react with other compounds or its capability to elicit a response in a biological read out system (e.g., induction of a reporter gene). Means which are capable of specifically recognizing the chemical structure of a metabolite are, preferably, antibodies or other proteins which specifically interact with chemical structures, such as receptors or enzymes. Specific antibodies, for instance, may be obtained using the metabolite as antigen by methods well known in the art. Antibodies as referred to herein include both polyclonal and monoclonal antibodies, as well as fragments thereof, such as Fv, Fab and $F(ab)_2$ fragments that are capable of binding the antigen or hapten. The present invention also includes humanized hybrid antibodies wherein amino acid sequences of a non-human donor antibody exhibiting a desired antigen-specificity are combined with sequences of a human acceptor antibody. Moreover, encompassed are single chain antibodies. The donor sequences will usually include at least the antigen-binding amino acid residues of the donor but may comprise other structurally and/or functionally relevant amino acid residues of the donor antibody as well. Such hybrids can be prepared by several methods well known in the art. Suitable proteins which are capable of specifically recognizing the metabolite are, preferably, enzymes which are involved in the metabolic conversion of the said metabolite. Said enzymes may either use the metabolite as a substrate or may convert a substrate into the metabolite. Moreover, said antibodies may be used as a basis to generate oligopeptides which specifically recognize the metabolite. These oligopeptides shall, for example, comprise the enzyme's binding domains or pockets for the said metabolite. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the metabolite may also be identified based on its capability to react with other compounds, i.e. by a specific chemical reaction. Suitable reactions are well known in the art and, preferably encompass enzymatic reactions (e.g for mannose Pitkanen E, Pitkanen O, Uotila L.; Eur J Clin Chem Clin Biochem. 1997 October; 35(10):761-6; or ascorbic acid Winnie Lee, Susan M. Roberts and Robert F. Labbe; *Clinical Chemistry* 43: 154-157, 1997), enzymatic spectrophotometric methods (BN La Du, RR Howell, P J Michael and E K Sober; Pediatrics, January 1963, 39-46, Vol 31, No. 1), spectrofluorimetric methods (Sumi T, Umeda Y, Kishi Y, Takahashi K, Kakimoto F.; Clin Chim Acta. 1976 Dec. 1; 73(2):233-9) and fluorescence; chemiluminescence (J. J. Thiele, H. J. Freisleben, J. Fuchs and F. R. Ochsendorf; Human Reproduction, Vol. 10, No. 1, pp. 110-115, 1995). Further detection methods such as capillary electrophoresis (Hubert A. Carchon and Jaak Jaeken; *Clinical Chemistry* 47: 1319-1321, 2001) and colorimetric methods (Kyaw A; Clin Chim Acta. 1978 June; 86(2):153-7) can be used. Further, the metabolite may be determined in a sample due to its capability to elicit a response in a biological read out system. The biological response shall be detected as read out indicating the presence and/or the amount of the metabolite comprised by the sample. The biological response may be, e.g., the induction of gene expression or a phenotypic response of a cell or an organism.

Further, it is to be understood that depending of the technique used for determining the said at least one metabolite, the analyte which will be detected could be a derivative of the physiologically occurring metabolite, i.e. the metabolite present within a subject. Such analytes may be generated as a result of sample preparation or detection means. The compounds referred to herein are deemed to be analytes. However, as set forth above, these analytes will represent the metabolites in a qualitative and quantitative manner. Moreover, it is to be understood that for a plurality of metabolites, the metabolite will be identical to the analyte.

The term "reference" refers to results, i.e. data of characteristic features of the at least one metabolite, which can be correlated to a predispostion for diabetes. Such reference results are, preferably, obtained from a sample from a subject known to have predisposition for diabetes. The reference results may be obtained by applying the method of the present invention. Alternatively, but nevertheless also preferred, the reference results may be obtained from sample of a subject known not to have a predisposition for diabetes, i.e. which will not develop diabetes in the future, and, more preferably, other diseases as well. Moreover, the reference, also preferably, could be a calculated reference, most preferably the average or median, for the relative or absolute amount of a metabolite of a population of individuals (comprising the subject to be investigated). The absolute or relative amounts of the metabolites of said individuals of the population can be determined as specified elsewhere herein. How to calculate a suitable reference value, preferably, the average or median, is well known in the art. The population of subjects referred to before shall comprise a plurality of subjects, preferably, at least 5, 10, 50, 100, 1,000 or 10,000 subjects. It is to be understood that the subject to be diagnosed by the method of the present invention and the subjects of the said plurality of subjects are of the same species.

More preferably, the reference results, i.e. values for at least one characteristic features of the at least one metabolite, will be stored in a suitable data storage medium such as a database and are, thus, also available for future diagnoses. This also allows efficiently diagnosing predisposition for a disease because suitable reference results can be identified in the database once it has been confirmed (in the future) that the subject from which the corresponding reference sample was obtained (indeed) developed diabetes. Preferred reference results which are associated with diabetes or predisposition therefor in humans are those shown in the Tables of the accompanying Examples.

The term "comparing" refers to assessing whether the results of the determination described hereinabove in detail, i.e. the results of the qualitative or quantitative determination of the at least one metabolite, are identical or similar to reference results or differ therefrom.

In case the reference results are obtained from a subject known to have a predisposition for diabetes, the said predisposition can be diagnosed based on the degree of identity or similarity between the test results obtained from the test sample and the aforementioned reference results, i.e. based on an identical or similar qualitative or quantitative composition with respect to the at least one metabolite. The results of the test sample and the reference results are identical, if the values for the characteristic features and, in the case of quantitative determination, the intensity values are identical. Said results are similar, if the values of the characteristic features are identical but the intensity values are different. Such a difference is, preferably, not significant and shall be characterized in that the values for the intensity are within at least the interval between $1^{st}$ and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value. the $50^{th}$, $60^{th}$, $70^{th}$, $80^{th}$, $90^{th}$ or $95^{th}$ percentile of the reference value.

In case the reference results are obtained from a subject or a group of subjects known not to have a predisposition for diabetes, the said predisposition can be diagnosed based on the differences between the test results obtained from the test sample and the aforementioned reference results, i.e. differences in the qualitative or quantitative composition with respect to the at least one metabolite. The same applies if a calculated reference as specified above is used. The difference may be an increase in the absolute or relative amount of a metabolite (sometimes referred to as up-regulation of the metabolite; see also Examples) or a decrease in either of said amounts or the absence of a detectable amount of the metabolite (sometimes referred to as up-regulation of the metabolite; see also Examples). Preferably, the difference in the relative or absolute amount is significant, i.e. outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, $1^{st}$ and $99^{th}$ percentile of the reference value. For the specific metabolites referred to in this specification elsewhere, preferred values for the changes in the relative amounts (i.e. "fold"-changes) or the kind of change (i.e. "up"- or "down"-regulation resulting in a higher or lower relative and/or absolute amount) are indicated in the accompanying Tables, below. If it is indicated in said tables that a given metabolite is "up-regulated" in a subject, the relative and/or absolute amount will be increased, if it is "down-regulated", the relative and/or absolute amount of the metabolite will be decreased. Moreover, the "fold"-change indicates the degree of increase or decrease, e.g., a 2-fold increase means that the amount is twice the amount of the metabolite compared to the reference.

Thus, the method of the present invention in a preferred embodiment includes a reference that is derived from a subject or a group known to have predisposition for diabetes. Most preferably, identical or similar results for the test sample and the said reference (i.e. similar relative or absolute amounts of the at least one metabolite) are indicative for a predisposition for diabetes in that case. In another preferred embodiment of the method of the present invention, the reference is derived from a subject or a group known not to have predisposition for diabetes or is a calculated reference. Most preferably, the absence of the at least one metabolite or an amount which, preferably significantly, differs in the test sample in comparison to the reference sample (i.e. a significant difference in the absolute or relative amount is observed) is indicative for a predisposition for diabetes in such a case.

The comparison is, preferably, assisted by automation. For example, a suitable computer program comprising algorithm for the comparison of two different data sets (e.g., data sets comprising the values of the characteristic feature(s)) may be used. Such computer programs and algorithm are well known in the art. Notwithstanding the above, a comparison can also be carried out manually.

The aforementioned methods for the determination of the at least one metabolite can be implemented into a device. A device as used herein shall comprise at least the aforementioned means. Moreover, the device, preferably, further comprises means for comparison and evaluation of the detected characteristic feature(s) of the at least one metabolite and, also preferably, the determined signal intensity. The means of the device are, preferably, operatively linked to each other. How to link the means in an operating manner will depend on the type of means included into the device. For example, where means for automatically qualitatively or quantitatively determining the metabolite are applied, the data obtained by said automatically operating means can be processed by, e.g., a computer program in order to facilitate the diagnosis. Preferably, the means are comprised by a single device in such a case. Said device may accordingly include an analyzing unit for the metabolites and a computer unit for processing the resulting data for the diagnosis. Alternatively, where means such as test stripes are used for determining the metabolites, the means for diagnosing may comprise control stripes or tables allocating the determined result data to result data known to be accompanied with a predisposition for diabetes or those being indicative for a subject without such a predisposition as discussed above. Preferred devices are those which can be applied without the particular knowledge of a specialized clinician, e.g., test stripes or electronic devices which merely require loading with a sample.

Alternatively, the methods for the determination of the at least one metabolite can be implemented into a system comprising several devices which are, preferably, operatively linked to each other. Specifically, the means must be linked in a manner as to allow carrying out the method of the present invention as described in detail above. Therefore, operatively linked, as used herein, preferably, means functionally linked. Depending on the means to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via LAN (Wireless LAN, WLAN). A preferred system comprises means for determining metabolites. Means for determining metabolites, as used herein, encompass means for separating metabolites, such as chromatographic devices, and means for metabolite determination, such as mass spectrometry devices. Suitable devices have been described in detail above. Preferred means for compound separation to be used in the system of the present invention include chromatographic devices, more preferably devices for liquid chromatography, HPLC, and/or gas chromatography. Preferred devices for compound determination comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF. The separation and determination means are, preferably, coupled to each other. Most preferably, LC-MS and/or GC-MS is used in the system of the present invention as described in detail elsewhere in the specification. Further comprised shall be means for comparing and/or analyzing the results obtained from the means for determination of metabolites. The means for comparing and/or analyzing the results may comprise at least one databases and an implemented computer program for comparison of the results. Preferred embodiments of the aforementioned systems and devices are also described in detail below.

Advantageously, it has been found in accordance with the present invention that the at least one of the aforementioned metabolites will be a suitable biomarker for a predisposition for diabetes. Applying these metabolites as biomarkers allows a rapid, reliable and cost-effective diagnosis of a predisposition for diabetes. Moreover, the method can be assisted by automation as described elsewhere in this description and, thus, allows high-throughput screening for subjects being at risk of suffering from diabetes. Thereby, the method of the present invention may assist health programs for diabetes prevention and can be used to monitor success of preventive therapies for diabetes or other measures for the prevention of diabetes including nutritional diets. Moreover, the metabolites or combinations of metabolites referred to herein can be determined simultaneously in a time and cost effective manner by the metabolic profiling techniques described in this specification. Furthermore, the method of the present invention allows to asses the risk for a subject for being or becoming a member of a certain diabetes risk group, i.e. IFG, IGT or IFG&IGT. The reported prevalence of IFG and IGT varies widely between 5 and 26° A) depending on ethnic group, age and sex distribution. Both risk groups, IFG and IGT are expected to increase in the near future. For both, IFG or IGT risk groups, a 25% progressing to incident diabetes is reported within 3-5 years, with 50% remaining in their abnormal glycemic state and 25% reverting to normal glucose levels. With longer observation; the majority of individuals with IFG or IGT appear to develop diabetes. Individuals with both IFG and IGT (IFG&IGT) have approximately double the rate of developing diabetes compared with subjects have either IFG or IGT (Nathan 2007, Diabetes Care 30(3): 753-759).

The explanations and interpretations of the terms made above apply accordingly to the other embodiments specified herein below.

In a preferred embodiment of the method of the present invention said at least one metabolite is selected from the group consisting of: diacylglyceride (C18:1,C18:2) and triacylglyceride (C16:0,C18:2,C18:2).

Each of said metabolites is a suitable biomarker by its own for the predisposition referred to herein. However, most preferably, a group of biomarkers including biomarkers of one of the aforementioned groups is to be determined by the method of the present invention. A group of biomarkers consists, preferably, of at least two, at least three, at least four and, preferably, up to all of the aforementioned biomarkers. Furthermore, it has been found in the study underlying the present invention that the metabolites of the aforementioned groups are particularly well-suited as biomarkers for a predisposition for diabetes in male individuals. Accordingly, the subject to be diagnosed in accordance with the present invention is in the context with the aforementioned preferred embodiment, more preferably a male subject.

As described above, in a preferred embodiment of the method of the present invention, said determining of the at least one metabolite comprises mass spectrometry (MS). Mass spectrometry as used herein encompasses all techniques which allow for the determination of the molecular weight (i.e. the mass) or a mass variable corresponding to a compound, i.e. a metabolite, to be determined in accordance with the present invention. Preferably, mass spectrometry as used herein relates to GC-MS, LC-MS, direct infusion mass spectrometry, FT-ICR-MS, CE-MS, HPLC-MS, quadrupole mass spectrometry, any sequentially coupled mass spectrometry such as MS-MS or MS-MS-MS, ICP-MS, Py-MS, TOF or any combined approaches using the aforementioned techniques. How to apply these techniques is well known to the person skilled in the art. Moreover, suitable devices are commercially available. More preferably, mass spectrometry as used herein relates to LC-MS and/or GC-MS, i.e. to mass spectrometry being operatively linked to a prior chromatographic separation step. More preferably, mass spectrometry as used herein encompasses quadrupole MS. Most preferably, said quadrupole MS is carried out as follows: a) selection of a mass/charge quotient (m/z) of an ion created by ionisation in a first analytical quadrupole of the mass spectrometer, b) fragmentation of the ion selected in step a) by applying an acceleration voltage in an additional subsequent quadrupole which is filled with a collision gas and acts as a collision chamber, selection of a mass/charge quotient of an ion created by the fragmentation process in step b) in an additional subsequent quadrupole, whereby steps a) to c) of the method are carried out at least once and analysis of the mass/charge quotient of all the ions present in the mixture of substances as a result of the ionisation process, whereby the quadrupole is filled with collision gas but no acceleration voltage is applied during the analysis. Details on said most preferred mass spectrometry to be used in accordance with the present invention can be found in WO 03/073464.

More preferably, said mass spectrometry is liquid chromatography (LC) MS and/or gas chromatography (GC) MS.

Liquid chromatography as used herein refers to all techniques which allow for separation of compounds (i.e. metabolites) in liquid or supercritical phase. Liquid chromatography is characterized in that compounds in a mobile phase are passed through the stationary phase. When compounds pass through the stationary phase at different rates they become separated in time since each individual compound has its specific retention time (i.e. the time which is required by the compound to pass through the system). Liquid chromatography as used herein also includes HPLC. Devices for liquid chromatography are commercially available, e.g. from Agilent Technologies, USA. Gas chromatography as applied in accordance with the present invention, in principle, operates comparable to liquid chromatography. However, rather than having the compounds (i.e. metabolites) in a liquid mobile phase which is passed through the stationary phase, the compounds will be present in a gaseous volume. The compounds pass the column which may contain solid support materials as stationary phase or the walls of which may serve as or are coated with the stationary phase. Again, each compound has a specific time which is required for passing through the column. Moreover, in the case of gas chromatography it is preferably envisaged that the compounds are derivatised prior to gas chromatography. Suitable techniques for derivatisation are well known in the art. Preferably, derivatisation in accordance with the present invention relates to methoxymation and trimethylsilylation of, preferably, polar compounds and transmethylation, methoxymation and trimethylsilylation of, preferably, non-polar (i.e. lipophilic) compounds.

Furthermore, the present invention relates to a data collection comprising characteristic values of at least one metabolite being indicative for a predisposition for diabetes, said metabolite being selected from any one of the groups referred to above.

The term "data collection" refers to a collection of data which may be physically and/or logically grouped together. Accordingly, the data collection may be implemented in a single data storage medium or in physically separated data storage media being operatively linked to each other. Preferably, the data collection is implemented by means of a database. Thus, a database as used herein comprises the data collection on a suitable storage medium. Moreover, the database, preferably, further comprises a database management system. The database management system is, preferably, a network-based, hierarchical or object-oriented database management system. Furthermore, the database may be a federal or integrated database. More preferably, the database will be implemented as a distributed (federal) system, e.g. as a Client-Server-System. More preferably, the database is structured as to allow a search algorithm to compare a test data set with the data sets comprised by the data collection. Specifically, by using such an algorithm, the database can be searched for similar or identical data sets being indicative for diabetes or a predisposition thereof (e.g. a query search). Thus, if an identical or similar data set can be identified in the data collection, the test data set will be associated with a predisposition for diabetes. Consequently, the information obtained from the data collection can be used to diagnose a predisposition for diabetes based on a test data set obtained from a subject. More preferably, the data collection comprises characteristic values of all metabolites comprised by any one of the groups recited above.

In light of the foregoing, the present invention encompasses a data storage medium comprising the aforementioned data collection.

The term "data storage medium" as used herein encompasses data storage media which are based on single physical entities such as a CD, a CD-ROM, a hard disk, optical storage media, or a diskette. Moreover, the term further includes data storage media consisting of physically separated entities which are operatively linked to each other in a manner as to provide the aforementioned data collection, preferably, in a suitable way for a query search.

The present invention also relates to a system comprising:
(a) means for comparing characteristic values of metabolites of a sample operatively linked to
(b) a data storage medium as described above.

The term "system" as used herein relates to different means which are operatively linked to each other. Said means may be implemented in a single device or may be physically separated devices which are operatively linked to each other. The means for comparing characteristic values of metabolites operate, preferably, based on an algorithm for comparison as mentioned before. The data storage medium, preferably, comprises the aforementioned data collection or database, wherein each of the stored data sets being indicative for a predisposition for diabetes. Thus, the system of the present invention allows identifying whether a test data set is comprised by the data collection stored in the data storage medium. Consequently, the system of the present invention may be applied as a diagnostic means in diagnosing a predisposition for diabetes.

In a preferred embodiment of the system, means for determining characteristic values of metabolites of a sample are comprised.

The term "means for determining characteristic values of metabolites" preferably relates to the aforementioned devices for the determination of metabolites such as mass spectrometry devices, NMR devices or devices for carrying out chemical or biological assays for the metabolites.

Moreover, the present invention relates to a diagnostic means comprising means for the determination of at least one metabolite selected from any one of the groups referred to above.

The term "diagnostic means", preferably, relates to a diagnostic device, system or biological or chemical assay as specified elsewhere in the description in detail.

The expression "means for the determination of at least one metabolite" refers to devices or agents which are capable of specifically recognizing the metabolite. Suitable devices may be spectrometric devices such as mass spectrometry, NMR devices or devices for carrying out chemical or biological assays for the metabolites. Suitable agents may be compounds which specifically detect the metabolites. Detection as used herein may be a two-step process, i.e. the compound may first bind specifically to the metabolite to be detected and subsequently generate a detectable signal, e.g., fluorescent signals, chemiluminescent signals, radioactive signals and the like. For the generation of the detectable signal further compounds may be required which are all comprised by the term "means for determination of the at least one metabolite". Compounds which specifically bind to the metabolite are described elsewhere in the specification in detail and include, preferably, enzymes, antibodies, ligands, receptors or other biological molecules or chemicals which specifically bind to the metabolites.

Further, the present invention relates to a diagnostic composition comprising at least one metabolite selected from any one of the groups referred to above.

The at least one metabolite selected from any of the aforementioned groups will serve as a biomarker, i.e. an indicator molecule for a risk condition in the subject, i.e. the predisposition of diabetes. Thus, the metabolite molecules itself may serve as diagnostic compositions, preferably, upon visualization or detection by the means referred to in herein. Thus, a diagnostic composition which indicates the presence of a metabolite according to the present invention may also comprise the said biomarker physically, e.g., a complex of an antibody and the metabolite to be detected may serve as the diagnostic composition. Accordingly, the diagnostic composition may further comprise means for detection of the metabolites as specified elsewhere in this description. Alternatively, if detection means such as MS or NMR based techniques are used, the molecular species which serves as an indicator for the risk condition will be the at least one metabolite comprised by the test sample to be investigated. Thus, the at least one metabolite referred to in accordance with the present invention shall serve itself as a diagnostic composition due to its identification as a biomarker.

Finally, the present invention relates to the use of at least one metabolite or means for the determination thereof for the manufacture of a diagnostic device or composition for diagnosing a predisposition for diabetes, wherein said at least one metabolite is selected from any one of the groups referred to above.

As specified above already, each of said metabolites is a suitable biomarker by its own for a predisposition of the diseases referred to herein. However, most preferably, a group of biomarkers including biomarkers of any one of the aforementioned groups is to be determined by the method of the present invention. A group of biomarkers consists, preferably, of at least two, at least three, at least four and, preferably, up to all of the aforementioned biomarkers.

All references referred to above are herewith incorporated by reference with respect to their entire disclosure content as well as their specific disclosure content explicitly referred to in the above description.

The invention will now be illustrated by the following Examples which are not intended to restrict or limit the scope of this invention.

EXAMPLE 1

Determination of Metabolites

Volunteers were informed about planed examinations. The experimental protocol was approved by the Dife (German Institute for Human Nutrition) Institutional Review Board, and all subjects gave written informed consent. Afterwards anthropometric values and intima media thickness were measured. Following these examinations an oral glucose tolerance test (OGTT) with 75 g glucose was performed. Blood samples were taken at 0, 30, 60 and 120 minutes. Volunteers were categorized by criteria of the WHO and ADA. Plasma was obtained from whole blood by addition of EDTA as anticoagulant and subsequent centrifugation.

Samples were prepared and subjected to LCMS and GCMS analysis as described in the following:

The samples were prepared in the following way: Proteins were separated by precipitation from blood plasma. After addition of water and a mixture of ethanol and dichlormethan the remaining sample was fractioned into an aqueous, polar phase and an organic, lipophilic phase.

For the transmethanolysis of the lipid extracts a mixture of 140 µl of chloroform, 37 µl of hydrochloric acid (37% by weight HCl in water), 320 µl of methanol and 20 µl of toluene was added to the evaporated extract. The vessel was sealed tightly and heated for 2 hours at 100° C., with shaking. The solution was subsequently evaporated to dryness. The residue was dried completely.

The methoximation of the carbonyl groups was carried out by reaction with methoxyamine hydrochloride (20 mg/ml in pyridine, 100 µl for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N-methyl-N-(trimethylsilyl)-2,2,2-trifluoroacetamide (MSTFA) was carried out for 30 minutes at 60° C., again in the tightly sealed vessel. The final volume before injection into the GC was 220 µl.

For the polar phase the derivatization was performed in the following way: The methoximation of the carbonyl groups was carried out by reaction with methoxyamine hydrochloride (20 mg/ml in pyridine, 50 µl for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N-methyl-N-(trimethylsilyl)-2,2,2-trifluoroacetamide (MSTFA) was carried out for 30 minutes at 60° C., again in the tightly sealed vessel. The final volume before injection into the GC was 110 µl.

The GC-MS systems consisted of an Agilent 6890 GC coupled to an Agilent 5973 MSD. The autosamplers are CompiPal or GCPal from CTC.

For the analysis usual commercial capillary separation columns (30 m×0.25 mm×0.25 µm) with different poly-methylsiloxane stationary phases containing 0% up to 35% of aromatic moieties, depending on the analysed sample materials and fractions from the phase separation step, were used (for example: DB-1 ms, HP-5 ms, DB-XLB, DB-35 ms, Agilent Technologies). Up to 1 µL of the final volume was injected splitless and the oven temperature program was started at 70° C. and ended at 340° C. with different heating rates depending on the sample material and fraction from the phase separation step in order to achieve a sufficient chromatographic separation and number of scans within each analyte peak. Furthermore RTL (Retention Time Locking, Agilent Technologies) was used for the analysis and usual GC-MS standard conditions, for example constant flow with nominal 1 to 1.7 ml/min. and helium as the mobile phase gas, ionisation was done by electron impact with 70 eV, scanning within a m/z range from 15 to 600 with scan rates from 2.5 to 3 scans/sec and standard tune conditions.

The HPLC-MS systems consists of an Agilent 1100 LC system (Agilent Technologies, Waldbronn, Germany) coupled with an API 4000 Mass spectrometer (Applied Biosystem/MDS SCIEX, Toronto, Canada). HPLC analysis was performed on commercially available reversed phase separation columns with C18 stationary phases (for example: GROM ODS 7 pH, Thermo Betasil C18). Up to 10 µL of the final sample volume was injected and separation was performed with gradient elution using methanol/water/formic acid or acetonitrile/water/formic acid gradients at a flowrate of 200 µL/min.

Mass spectrometry was carried out by electrospray ionisation in positive mode for the non-polar fraction and negative mode for the polar fraction using multiple-reaction monitoring-(MRM)-mode and fullscan from 100-1000 amu.

EXAMPLE 2

Data Evaluation

The GC- and LC-MS measurements of all blood plasma samples of risk subjects (subjects with high risk of developing diabetes; either "IFG": non-diabetes subjects with IFG positive, "IGT": non-diabetes subjects with IGT positive, or "IFG&IGT": non-diabetes subjects with IFG and IGT positives) and control subjects were conducted together with pooled plasma references. For each measurement batch, relative signal ratios of single subjects were calculated.

Risk-specific metabolites were determined by linear modeling of metabolite signal ratios by the ternary factor risk (levels: IFG,IGT,IFG&IGT) correcting for confounding factors age and BMI (body mass index) and also incorporating the two different genders: first a linear model with the just mentioned factors was generated, second estimated effects were evaluated by t-statistics, third only metabolites were selected with t-statistics p-value <0.05 concerning risk factor levels and interactions between gender and risk factor levels. Furthermore, regulation type was determined for each metabolite as "up" for increased ratios >1 of the respective risk level vs. control and "down" for decreased ratios <1 of risk level vs. control.

In the following Tables 1 to 5, the results of the data evaluation are presented. Tables 1 and 2 show the results for metabolites which have not yet been reported for diabetes patients. The metabolites referred to in Tables 3 to 5 have been described already for diabetes patients. Tables 1 and 3 list metabolites significant with regard to main effect "risk", specifying the respective significant factor levels IFG, IGT, and IFG&IGT (t-statistics). Tables 2, 4 and 5 list metabolites significant with regard to interaction of risk and gender, i.e., metabolites showing sex-specific differential regulation between controls and risk subjects. The results presented in the tables are ranked according to their potential and efficacy as biomarkers for diabetes or a predisposition thereof. The observed kind of regulation is also indicated. "Up" refers to an increase in the absolute or relative amount of the metabolite, while "down" refers to a decrease in said absolute or relative amount or even the absence of the metabolite in detectable amounts. Metabolites being particularly strong associated with diabetes are subdivided into groups indicated by the dividing lines in the Tables. Moreover, the risk group is indicated in the tables, i.e. IFG, IGT or IFG&IGT.

TABLE 1

Overall results. Metabolites differing significantly (p < 0.05) between risk groups for Diabetes mellitus type 2 (IFG, IGT and IFG&IGT) and controls (significant main effect "risk", i.e. same regulation type ("up", "down") in males and females.). Metabolites sorted by p-value. [IFG = Impaired Fasting Glucose; IGT = Impaired Glucose Tolerance; IFG&IGT: patients having both IFG and IGT]

| metabolite | regulation | risk_group |
| --- | --- | --- |
| cryptoxanthin | down | IGT |
| 2-hydroxy-palmitic acid | up | IFG |
| triacylglyceride (C16:0, C18:1, C18:2) | up | IGT |
| gondoic acid | up | IGT |
| tricosanoic acid | down | IFG&IGT |
| 5-Oxoproline | up | IFG |

TABLE 2

Metabolites differing specifically between male controls and male patients from risk groups for Diabetes. Metabolites differing significantly (p < 0.05) with regard to interaction risk-gender, i.e. differently regulated in males and females with regard to risk for Diabetes mellitus type 2 (IFG, IGT and IFG&IGT) and controls. Metabolites sorted by p-value. [IFG = Impaired Fasting Glucose; IGT = Impaired Glucose Tolerance; IFG&IGT: patients having both IFG and IGT]

| metabolite | reg_male | risk_group |
| --- | --- | --- |
| diacylglyceride (C18:1, C18:2) | down | IGT |
| triacylglyceride (C16:0, C18:2, C18:2) | down | IGT |
| triacylglyceride (C16:0, C18:1, C18:2) | down | IFG |

TABLE 3

Overall results. Metabolites differing significantly (p < 0.05) between risk groups for Diabetes mellitus type 2 (IFG, IGT and IFG&IGT) and controls (significant main effect "risk", i.e. same regulation type ("up", "down") in males and females.). Metabolites sorted by p-value. [IFG = Impaired Fasting Glucose; IGT = Impaired Glucose Tolerance; IFG&IGT: patients having both IFG and IGT]

| metabolite | regulation | risk_group |
| --- | --- | --- |
| lactate | up | IFG |
| alpha-ketoisocaproic acid | down | IGT |
| glucose | up | IFG&IGT |
| methionine | down | IGT |
| mannose | up | IFG&IGT |
| 3-hydroxybutyric acid | up | IGT |
| leucine | up | IGT |
| uric acid | up | IFG |
| threonic acid | up | IFG |
| beta-carotene | down | IFG&IGT |
| ascorbic acid | up | IFG&IGT |
| glycine | down | IGT |
| triacylglycerides | down | IFG |
| lactate | up | IGT |
| phospholipids | up | IGT |
| creatinine | down | IGT |
| glutamate | up | IFG |
| alpha-ketoisocaproic acid | down | IFG&IGT |
| triacylglycerides | up | IGT |
| valine | up | IGT |
| malate | up | IFG |
| alpha-ketoisocaproic acid | down | IFG |
| isoleucine | up | IGT |
| succinate | up | IFG |
| glucose-1-phosphate | up | IFG&IGT |
| valine | up | IFG&IGT |
| eicosapentaenoic acid (C20:cis[5, 8, 11, 14, 17]5) | down | IFG&IGT |
| phospholipids | up | IFG |
| uric acid | up | IFG&IGT |
| citrate | up | IGT |
| aspargine | down | IFG&IGT |
| methionine | down | IFG |
| glutamine | down | IGT |
| palmitic acid | up | IGT |
| tryptophane | down | IFG&IGT |
| alanine | up | IGT |
| glutamate | up | IGT |
| citrulline | down | IGT |
| cholestenol | down | IFG&IGT |
| threonine | down | IGT |
| ornithine | up | IFG |
| arginine | down | IGT |
| mannose | up | IFG |
| 3-hydroxybutyric acid | up | IFG&IGT |
| glutamine | down | IFG |
| pregnenolone sulfate | up | IFG&IGT |
| glyceric acid | up | IGT |
| folate | up | IFG |
| malate | up | IGT |
| beta-carotene | down | IFG |

TABLE 3-continued

Overall results. Metabolites differing significantly (p < 0.05) between risk groups for Diabetes mellitus type 2 (IFG, IGT and IFG&IGT) and controls (significant main effect "risk", i.e. same regulation type ("up", "down") in males and females.). Metabolites sorted by p-value. [IFG = Impaired Fasting Glucose; IGT = Impaired Glucose Tolerance; IFG&IGT: patients having both IFG and IGT]

| metabolite | regulation | risk_group |
|---|---|---|
| leucine | up | IFG |
| glutamine | down | IFG&IGT |
| alpha-tocopherol | up | IFG&IGT |
| myo-inositol | up | IFG |
| stearic acid | up | IGT |
| glycerol-3-phosphate | up | IFG |
| beta-carotene | down | IGT |

TABLE 4

Metabolites differing specifically between male controls and male patients from risk groups for Diabetes. Metabolites differing significantly (p < 0.05) with regard to interaction risk-gender, i.e. differently regulated in males and females with regard to risk for Diabetes mellitus type 2 (IFG, IGT and IFG&IGT) and controls. Metabolites sorted by p-value. [IFG = Impaired Fasting Glucose; IGT = Impaired Glucose Tolerance; IFG&IGT: patients having both IFG and IGT]

| metabolite | reg_male | risk_group |
|---|---|---|
| tryptophane | down | IGT |
| alanine | down | IFG |
| leucine | down | IGT |
| palmitic acid | down | IFG |
| eicosatrienoic acid | down | IGT |
| glycerophospholipids | down | IGT |
| isoleucine | down | IFG |
| eicosatrienoic acid | down | IFG |
| tryptophane | down | IFG |
| lignoceric acid | down | IGT |
| linoleic acid | down | IGT |
| serine | up | IFG |
| tyrosine | down | IGT |
| linoleic acid | down | IFG |
| pregnenolone sulfate | down | IGT |
| aspartate | up | IGT |
| arachidonic acid | down | IGT |
| succinate | up | IFG&IGT |

TABLE 5

Metabolites differing specifically between female controls and female patients from risk groups for Diabetes. Metabolites differing significantly (p < 0.05) with regard to interaction risk-gender, i.e. differently regulated in males and females with regard to risk for Diabetes mellitus type 2 (IFG, IGT and IFG&IGT) and controls. Metabolites sorted by p-value. [IFG = Impaired Fasting Glucose; IGT = Impaired Glucose Tolerance; IFG&IGT: patients having both IFG and IGT]

| metabolite | reg_female | risk_group |
|---|---|---|
| alanine | up | IFG |
| palmitic acid | up | IFG |
| isoleucine | up | IFG |
| eicosatrienoic acid | up | IFG |
| uric acid | up | IFG |
| stearic acid | up | IFG |
| serine | down | IFG |

The invention claimed is:

1. A method for diagnosing a predisposition for diabetes comprising:
   (a) determining at least one metabolite in a test sample of a subject suspected to have a predisposition for diabetes, said at least one metabolite selected from the group consisting of gondoic acid and tricosanoic acid to obtain test results; and
   (b) comparing the test results of the determination in step (a) to a reference, whereby a predisposition for diabetes is to be diagnosed.

2. The method of claim 1, wherein at least one additional metabolite is determined and is selected from the group consisting of diacylglyceride (C18:1,C18:2) and triacylglyceride (C16:0,C18:2,C18:2).

3. The method of claim 2, wherein said subject is a male.

4. The method of claim 1, wherein said determining the said at least one metabolite comprises mass spectrometry (MS).

5. The method of claim 4, wherein said mass spectrometry is liquid chromatography (LC) MS and/or gas chromatography (GC) MS.

6. The method of claim 5, wherein the metabolite is gondoic acid.

7. The method of claim 5, wherein the metabolite is tricosanoic acid.

8. The method of claim 1, wherein said reference is derived from a subject known to have a predisposition for diabetes.

9. The method of claim 8, wherein identical or similar results for the test sample and the reference are indicative for a predisposition for diabetes.

10. The method of claim 1, wherein said reference is derived from a subject known to have no predisposition for diabetes.

11. The method of claim 10, wherein the absence of the said at least one metabolite or an amount thereof which differs in the test sample in comparison to the reference sample is indicative for a predisposition for diabetes.

12. The method of claim 1, wherein said reference is a calculated reference for the said at least one metabolite in a population of subjects.

13. The method of claim 12, wherein the absence of the said at least one metabolite or an amount thereof which differs in the test sample in comparison to the reference sample is indicative for a predisposition for diabetes.

14. The method of claim 1, wherein said sample is a sample of a body fluid of said subject.

15. The method of claim 1, wherein said subject is a human.

16. The method of claim 1, wherein at least one additional metabolite is determined selected from the group consisting of:
   (i) a long-chain saturated fatty acid,
   (ii) a poly-unsaturated fatty acid,
   (iii) an amino acid,
   (iv) an antioxidant,
   (v) a metabolite of the Citric Acid Cycle,
   (vi) a metabolite of the Urea Cycle,
   (vii) Mannose, alpha-Ketoisocaproic acid, Glycerol, lipid fraction, or 3-Hydroxybutyric acid, and
   (viii) glucose.

17. The method of claim 16, wherein the long chain saturated fatty acid is selected from the group consisting of Lignoceric acid (C24:0) and Melissic acid (C30:0).

18. The method of claim 16, wherein the poly-unsaturated fatty acid is selected from the group consisting of Docosahexaenoic acid (C22:eis[4,7,10,13,16,19]6), Eicosapentaenoic acid (C20:cis[5,8,11,14,17]5), Arachidonic acid (C20:cis-[5,8,11,14]4), Linoleic acid (C18:cis[9,12]2), and Linolenic acid (C18:cis[9,12,15]3).

19. The method of claim 16, wherein the amino acid is selected from the group consisting of Lysine, Alanine, Threonine, Tryptophane, Valine, Isoleucine, Leucine, Cysteine, Methionine, Tyrosine, Phenylalanine, Glycine, Proline, and Glutamine.

20. The method of claim 16, wherein the antioxidant is selected from the group consisting of Ascorbic acid, Coenzyme Q10, and alpha-Tocopherol.

21. The method of claim 16, wherein the metabolite of the Citric Acid Cycle is selected from the group consisting of Pyruvate, Citrate, and Malate.

22. The method of claim 16, wherein the metabolite of the Urea cycle is selected from the group consisting of Urea, Citrulline, Succinate, and Ornithine.

23. The method of claim 1, wherein at least one additional metabolite is determined selected from the group consisting of: 3-hydroxybutyric acid, alanine, alpha-ketoisocaproic acid, alpha-tocopherol, arginine, ascorbic acid, aspargine, beta-carotene, cholestenol, citrate, citrulline, creatinine, eicosapentaenoic acid (C20:cis[5,8,11,14,17]5), folate, glucose, glucose-1-phosphate, glutamate, glutamine, glyceric acid, glycerol-3-phosphate, glycine, isoleucine, lactate, leucine, malate, mannose, methionine, myo-inositol, ornithine, palmitic acid, phospholipids, pregnenolone sulfate, stearic acid, succinate, threonic acid, threonine, triacylglycerides, tryptophane, uric acid, and valine.

* * * * *